(12) United States Patent
Heine et al.

(10) Patent No.: US 10,590,996 B2
(45) Date of Patent: Mar. 17, 2020

(54) MEDICAL HANDLE WITH PNEUMATIC SAFETY COUPLING

(71) Applicants: Aesculap AG, Tuttlingen (DE); Rotomed AG, Bellach (CH)

(72) Inventors: Wolfgang Heine, Immendingen (DE); Edgar Blust, Königsfeld (DE); Thomas Müller, Bellach (CH); Frederick Lenzenhuber, Tuttlingen (DE); Anette Hildebrand, Brigachtal (DE); Simone Hermle, VS-Villingen (DE); Uwe Mattes, Tuttlingen (DE)

(73) Assignees: Aesculap AG (DE); Rotomed AG (CH)

( * ) Notice: Subject to any disclaimer, the term of this patent is extended or adjusted under 35 U.S.C. 154(b) by 341 days.

(21) Appl. No.: 15/540,475

(22) PCT Filed: Dec. 23, 2015

(86) PCT No.: PCT/EP2015/081208
§ 371 (c)(1),
(2) Date: Jun. 28, 2017

(87) PCT Pub. No.: WO2016/107814
PCT Pub. Date: Jul. 7, 2016

(65) Prior Publication Data
US 2017/0363157 A1 Dec. 21, 2017

(30) Foreign Application Priority Data

Dec. 29, 2014 (DE) .................. 10 2014 119 679

(51) Int. Cl.
*F16D 28/00* (2006.01)
*F16D 23/12* (2006.01)
(Continued)

(52) U.S. Cl.
CPC ............ *F16D 23/12* (2013.01); *A61B 17/162* (2013.01); *B25F 5/02* (2013.01); *F16D 25/12* (2013.01);
(Continued)

(58) Field of Classification Search
CPC ........ F16D 23/12; F16D 41/066; F16D 25/12; F16D 28/00; F16D 41/04; F16D 41/061;
(Continued)

(56) References Cited

U.S. PATENT DOCUMENTS 3,752,241 A 8/1973 Bent
6,520,976 B1 * 2/2003 Gage .................. A61B 17/1626
606/170

(Continued)

FOREIGN PATENT DOCUMENTS

| CN | 203042385 U | 7/2013 |
|---|---|---|
| EP | 1302282 A2 | 4/2003 |
| EP | 2532316 A2 | 12/2012 |

OTHER PUBLICATIONS

European Examination Report for European Application No. 15816201.6, dated May 24, 2018 with translation, 11 pages.
(Continued)

*Primary Examiner* — David J Hlavka
(74) *Attorney, Agent, or Firm* — RatnerPrestia

(57) ABSTRACT

A medical handle for pneumatically or hydraulically driven medical instruments or motor units includes a clutch member for mechanical and pneumatic/hydraulic coupling of a corresponding clutch member and a manually operable valve mechanism for selective pressurization of a medical instrument coupled thereto or the motor unit thereof, the valve mechanism being provided with a safety device for preventing pressurization in the case of an uncoupled medical instrument or the motor unit thereof. The clutch member
(Continued)

Figure 1A:
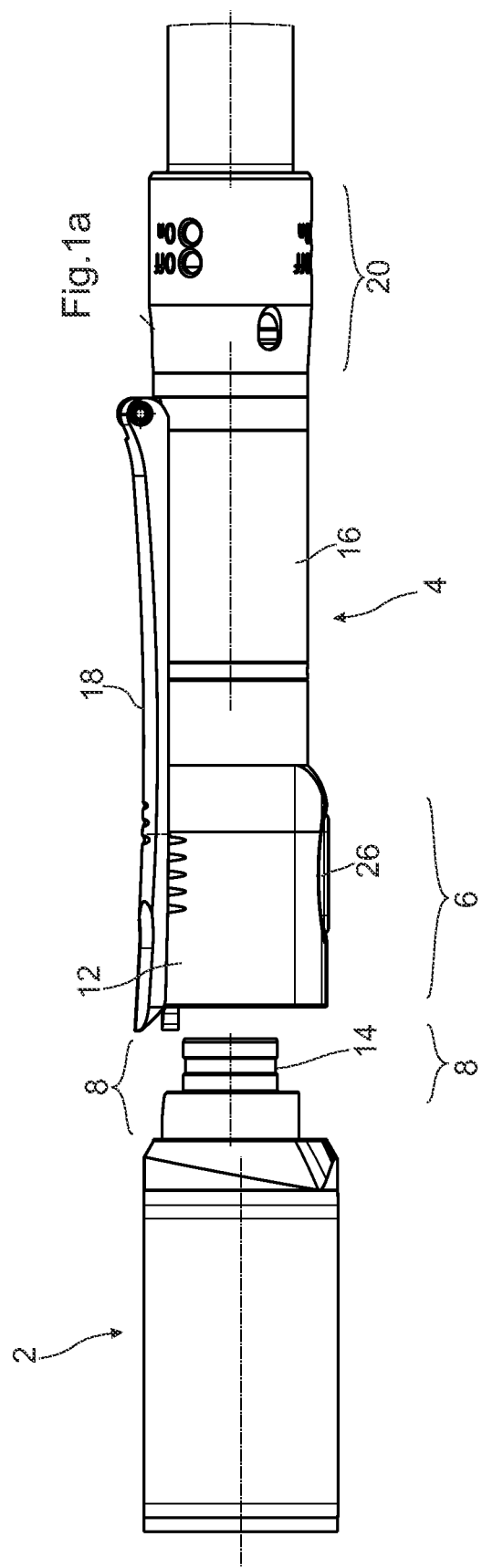

present on the side of the handle is provided to interact with the valve mechanism such that during or by the mechanical coupling operation the latter is automatically opened and/or enabled for manual opening, whereas in the uncoupled state the valve mechanism is closed and/or enabling is cancelled.

15 Claims, 8 Drawing Sheets

(51) Int. Cl.
*A61B 17/16* (2006.01)
*B25F 5/02* (2006.01)
*F16D 25/12* (2006.01)
*F16D 41/04* (2006.01)
*F16D 41/061* (2006.01)
*F16D 41/066* (2006.01)
*A61B 17/00* (2006.01)
*A61B 90/00* (2016.01)

(52) U.S. Cl.
CPC ............ *F16D 28/00* (2013.01); *F16D 41/04* (2013.01); *F16D 41/061* (2013.01); *F16D 41/066* (2013.01); *A61B 17/1622* (2013.01); *A61B 17/1628* (2013.01); *A61B 2017/0046* (2013.01); *A61B 2017/00367* (2013.01); *A61B 2017/00477* (2013.01); *A61B 2017/00539* (2013.01); *A61B 2017/00544* (2013.01); *A61B 2090/0808* (2016.02); *A61B 2090/0818* (2016.02)

(58) Field of Classification Search
CPC ............... B25F 5/02; A61B 17/162; A61B 2017/00477; A61B 2090/0818; A61B 2090/0808; A61B 2017/00544; A61B 2017/00539; A61B 2017/0046; A61B 2017/00367; A61B 17/1628; A61B 17/1622
See application file for complete search history.

(56) References Cited

U.S. PATENT DOCUMENTS

| | | | |
|---|---|---|---|
| 2002/0029812 A1* | 3/2002 | Hotta | F16K 1/443 137/613 |
| 2004/0099318 A1 | 5/2004 | Mikya et al. | |
| 2008/0115848 A1* | 5/2008 | Bruck | F15B 13/024 137/613 |
| 2008/0190636 A1 | 8/2008 | Tanner | |
| 2012/0316576 A1 | 12/2012 | Mahaffey et al. | |
| 2015/0107628 A1 | 4/2015 | Mahaffey et al. | |

OTHER PUBLICATIONS

International Search Report and Written Opinion for International Application No. PCT/EP2015/081208, dated Mar. 9, 2016—12 Pages.
German Search Report for German Application No. 10 2014 119 679.1, dated Oct. 14, 2015—13 Pages wtih English Translation.
Chinese Office Action for Chinese Application No. 201580071777.X, dated Aug. 12, 2019 with translation, 17 pages.

* cited by examiner

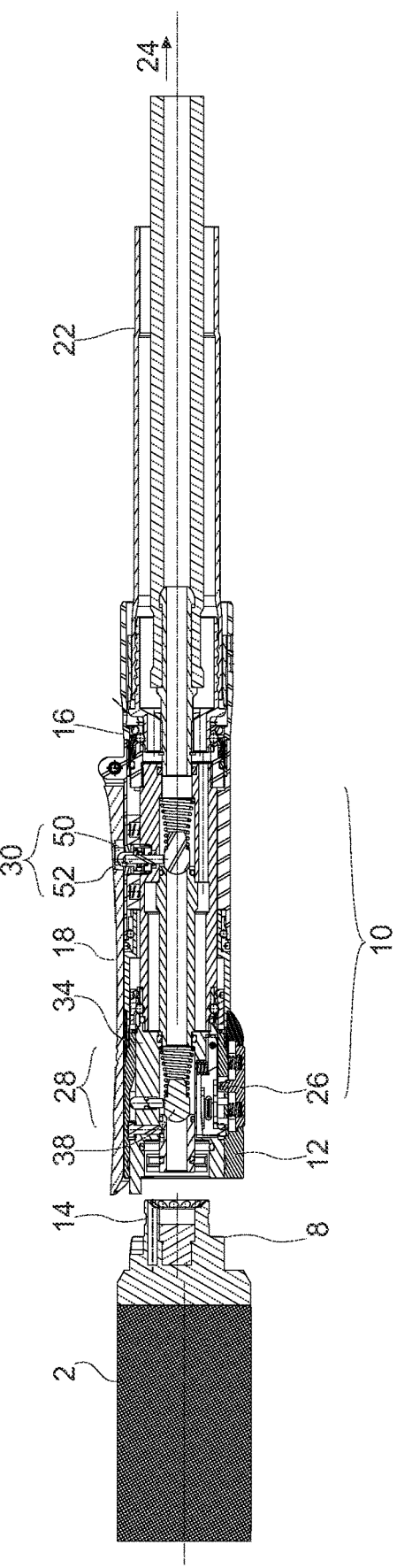

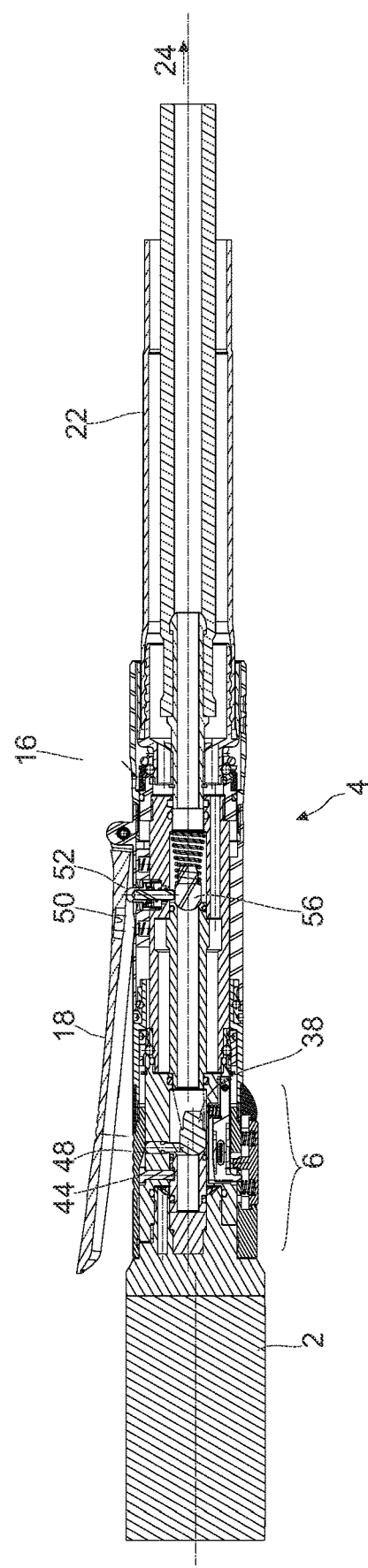

MEDICAL HANDLE WITH PNEUMATIC SAFETY COUPLING

RELATED APPLICATIONS

This application is the United States national phase of International Application No. PCT/EP2015/081208, filed Dec. 23, 2015, which is related to and claims the benefit of priority of German Application No. DE 10 2014 119 679.1, filed Dec. 29, 2014. The contents of International Application No. PCT/EP2015/081208 and German Application No. DE 10 2014 119 679.1 are incorporated by reference herein in their entireties.

FIELD

The present invention relates to a handle of medical instruments comprising an integrated pneumatic/hydraulic safety clutch.

BACKGROUND

Medical, especially surgical instruments relate, inter alia, to those instruments that are or can be equipped with motor-driven tools such as milling tools, drills, screwdrivers etc. The drive, for example for rotary or lifting motion of the tool, can be performed by an electric motor, hydraulically or pneumatically. Especially in the latter case, the instrument is connected to a compressed air source by means of which for example a turbine inside the instrument or as a separate motor unit is pressurized selectively and possibly controlled with compressed air, the rotation of the turbine then being transmitted directly or indirectly via a gear unit to the tool.

However, such pneumatically or hydraulically operated instruments are not permanently tightly connected to the pressurizing medium source but may arbitrarily be connected to or separated from the pressurizing medium source. For this purpose, clutches are required by means of which the instruments can be selectively connected pneumatically or hydraulically to the pressurizing medium source. Especially in surgical medicine, high requirements in terms of safety are made to said clutches so as to exclude injuries of patients and to facilitate handling of the instruments to the surgeon.

From the state of the art, medical, preferably surgical instrument systems comprising a pneumatic tool drive are known, as also the applicants in the present case have distributed them for years.

Such instrument systems usually include a pressurized medium source (to simplify matters, hereinafter referred to as pneumatic source) to which a preferably flexible pressure hose is or can be connected. At the downstream free end of the pressure hose there is preferably fixedly (i.e. permanently) mounted an operating handle configured as an actuating and/or control unit in the form of a handle at the distal free end of which in turn a clutch for a medical/surgical instrument is configured. The clutch takes over the mechanical connection between the handle and the selected instrument and, at the same time, the pneumatic connection of a pneumatic motor (e.g. turbine), which is internal to the instrument or separate, to a pneumatic actuating and/or control unit which is internal to the handle.

The actuating and/or control unit is composed of a manually operable actuator preferably in the form of an actuating lever pivoted on the handle and/or at least one press button, wherein the actuator mechanically acts directly or indirectly in a pneumatically/hydraulically pilot-controlled manner upon a regulating/control valve mechanism inside the handle which mechanism releases or inhibits a pneumatic connection to the instrument in response to the current actuating state. The release may be performed either according to the on-off principle or in a dosed manner corresponding to the degree of actuation of the actuator.

Since usually the handle is already connected to the pneumatic source and thus is pressurized before a selected instrument is coupled to the handle, there is basically the risk of the actuator being inadvertently actuated and, thus, of compressed air being allowed to escape in an uncontrolled manner. Moreover, there may arise the problem that, when the actuator is inadvertently actuated, the currently selected instrument is coupled which then is pressurized with compressed air and thus driven in an uncontrolled and inadvertent manner.

Therefore, in the known prior art at/within the handle a separate pneumatic safety lock is provided which after coupling the instrument and, resp., an upstream motor to the handle (and thus to the pressure hose—compressed air is applied) has to be manually enabled so as to release the function of the actuator. Such pneumatic safety lock may be, for example, an actuator latch which can be actuated by means of a slide supported on the preferably lever-shaped actuator so as to lock and/or unlock the actuator.

Although the afore-mentioned drawbacks and risks can be avoided by said additional pneumatic safety lock, handling of the instrument during surgical operation may possibly be complicated.

SUMMARY

In view of the afore-described state of the art, it is the general object of the present invention to further develop the afore-described medical handle (including the technical features already mentioned in this context) as well as the medical instrument system comprising the handle and the instrument and/or the drive motor unit for the instrument such that in this way high functional and/or operational safety is guaranteed without the handling being unduly impeded.

A clutch composed of a male part, preferably on the side of the surgical instrument and, resp., the motor unit, and a female part, preferably on the side of the handle, interacts in the area of the handle with the valve mechanism or, resp., regulating/control valve mechanism inside the handle which is (automatically/forcedly) opened during or by the mechanical coupling operation itself and/or is enabled for (manual) opening, whereas in the uncoupled state the valve mechanism or, resp., regulating/control valve mechanism is closed and/or enabling is cancelled. In this way, the arrangement of a pneumatic safety lock which has to be separately actuated is unnecessary and handling is facilitated. At the same time, the functional and/or operational safety is improved.

The afore-mentioned aspects can be technically materialized by two measures which can be provided each individually or in combination inside the handle.

As a first measure, the (female) clutch member on the side of the handle can be provided with and, resp., operatively connected to a first valve device of the valve mechanism or, resp., regulating/control valve mechanism which valve device is designed so that it is forcedly opened by/during pressure-tight locking of the clutch at the latest (via a first motion transmission train). As a second additional or alternative measure, the (female) clutch member on the side of the handle can interact with a second manually operable valve device of the valve mechanism or, resp., regulating/control valve mechanism of the handle (via a second motion transmission train) in such manner that the second valve device is functioning in the coupled and preferably locked state only and is not functioning in the uncoupled state (with the instrument/motor unit being removed) and therefore cannot be manually opened any longer.

The latter preferably can be achieved by the fact that proper functioning of the preferably lever-shaped actuator is simultaneously (forcedly/automatically) established especially by/upon locking the clutch on the side of the handle and, resp., the actuator is (forcedly/automatically) put out of function by unlocking the clutch and/or uncoupling the instrument/motor unit.

A simple constructional solution of the two afore-mentioned measures basically provides to operatively connect a manually operable clutch locking element movably supported on the handle (mechanically via the first motion transmission train) to the first valve device and/or (mechanically via the second motion transmission train) to the actuator of the second valve device so that manual operation of the clutch locking element automatically causes the first valve device to open/close and, resp., exerts a corresponding effect on the functioning of the actuator, for example by moving the actuator to a position in which the operative connection to a valve is interrupted or established, resp., or a (mechanical) latch is moved into or out of the actuating path of the actuator.

The first motion transmission train may include, for example, an axially displaceable actuating pin which can be actuated by the clutch locking element and toggles the first valve device between its open and closed positions in response to the actuating situation of the clutch locking element. The second motion transmission train may be, for example, an axially displaceable sleeve or push rod which is mechanically coupled to the support of the actuator and in this way axially displaces the support of the actuator in response to the actuating situation of the clutch locking element.

This constructional configuration additionally offers the option to equip the clutch locking element with plural (axial) actuating positions, for example a first actuating position (unlocking position) for uncoupling the handle and the instrument/motor unit, a second actuating position (active locking position) for locking the clutch while simultaneously opening the first valve device and putting the second valve device into function and a third actuating position (passive locking position) for locking the clutch while simultaneously opening the first valve device and putting the second valve device out of function. Providing the third actuating position in turn offers the possibility of arranging sort of an emergency stop switch during actuation of which the clutch locking element is preferably automatically (due to proper bias) shifted to the third actuating position (which is preferably located in the actuating path between the first and second actuating positions).

The clutch locking element preferably may be a cap sleeve which in the locking position radially encompasses clutch-side engaging or clamping elements and fixes the latter in the locked position.

BRIEF DESCRIPTION OF THE DRAWING FIGURES

Figure 1B:
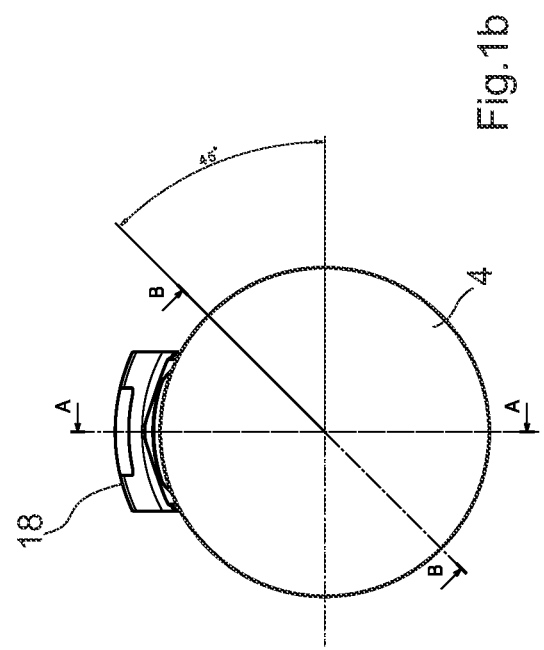
Figure 3A:
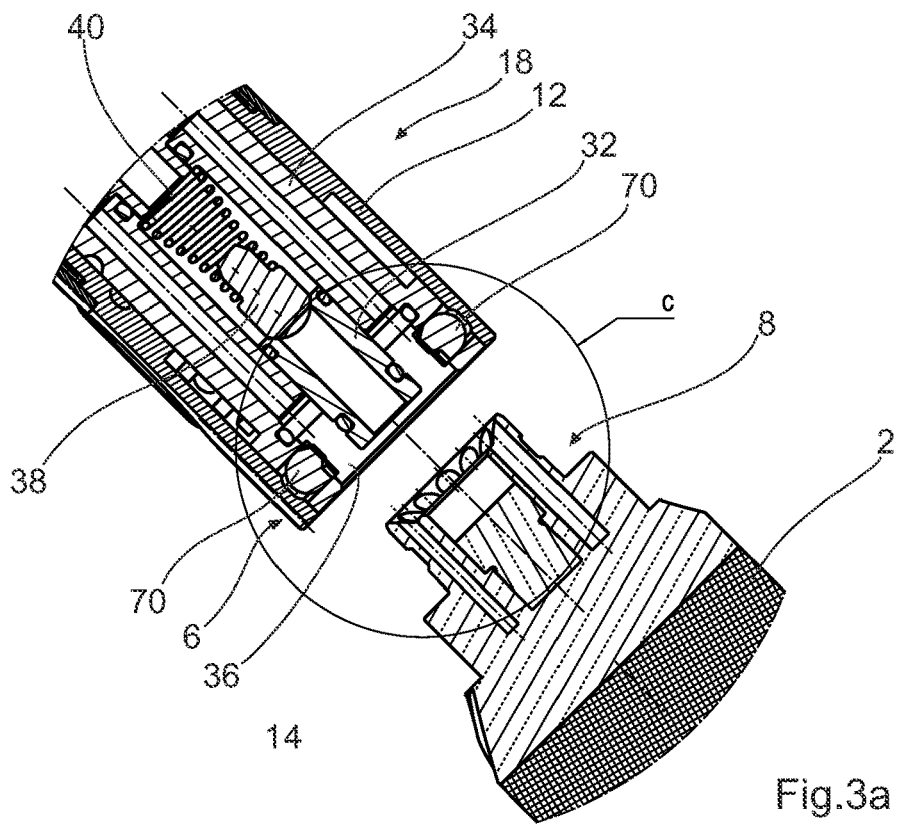
Figure 3B:
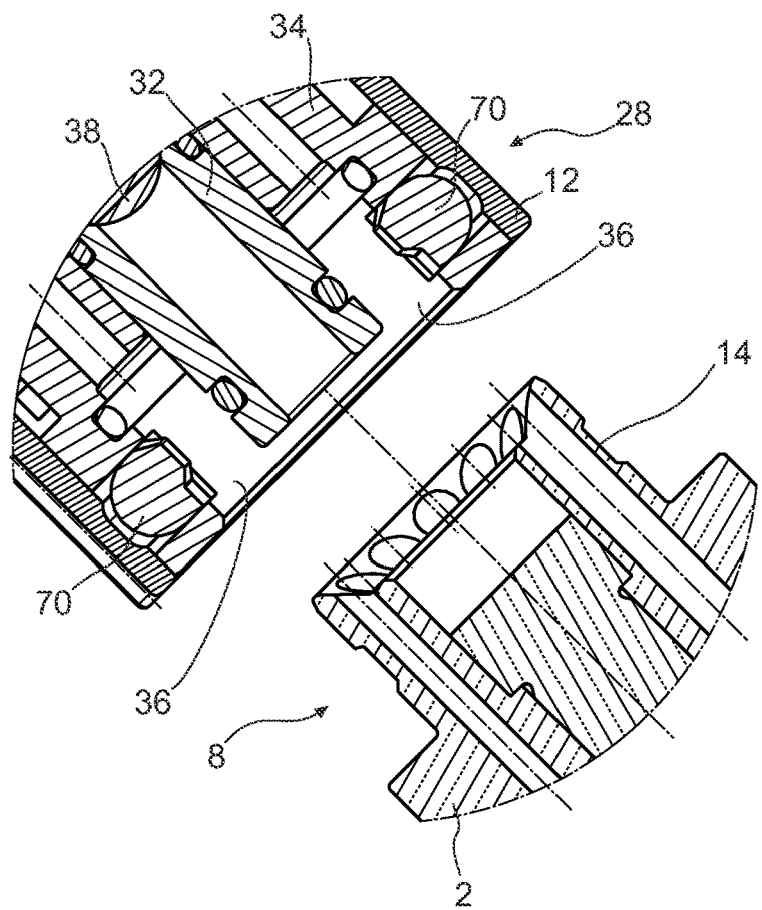
Figure 5A:
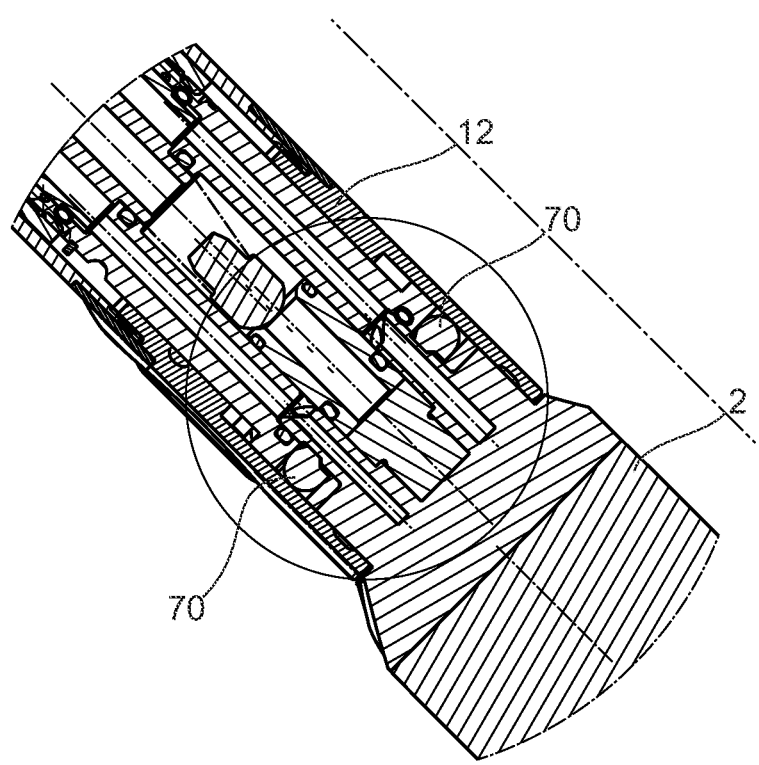
Figure 5B:
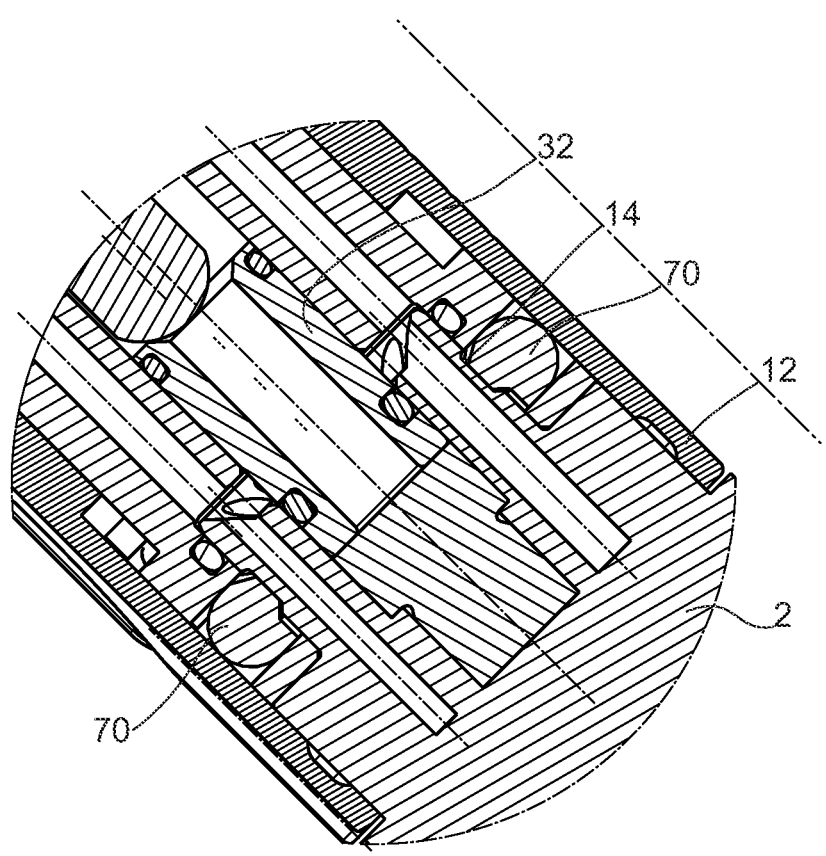
Figure 6:
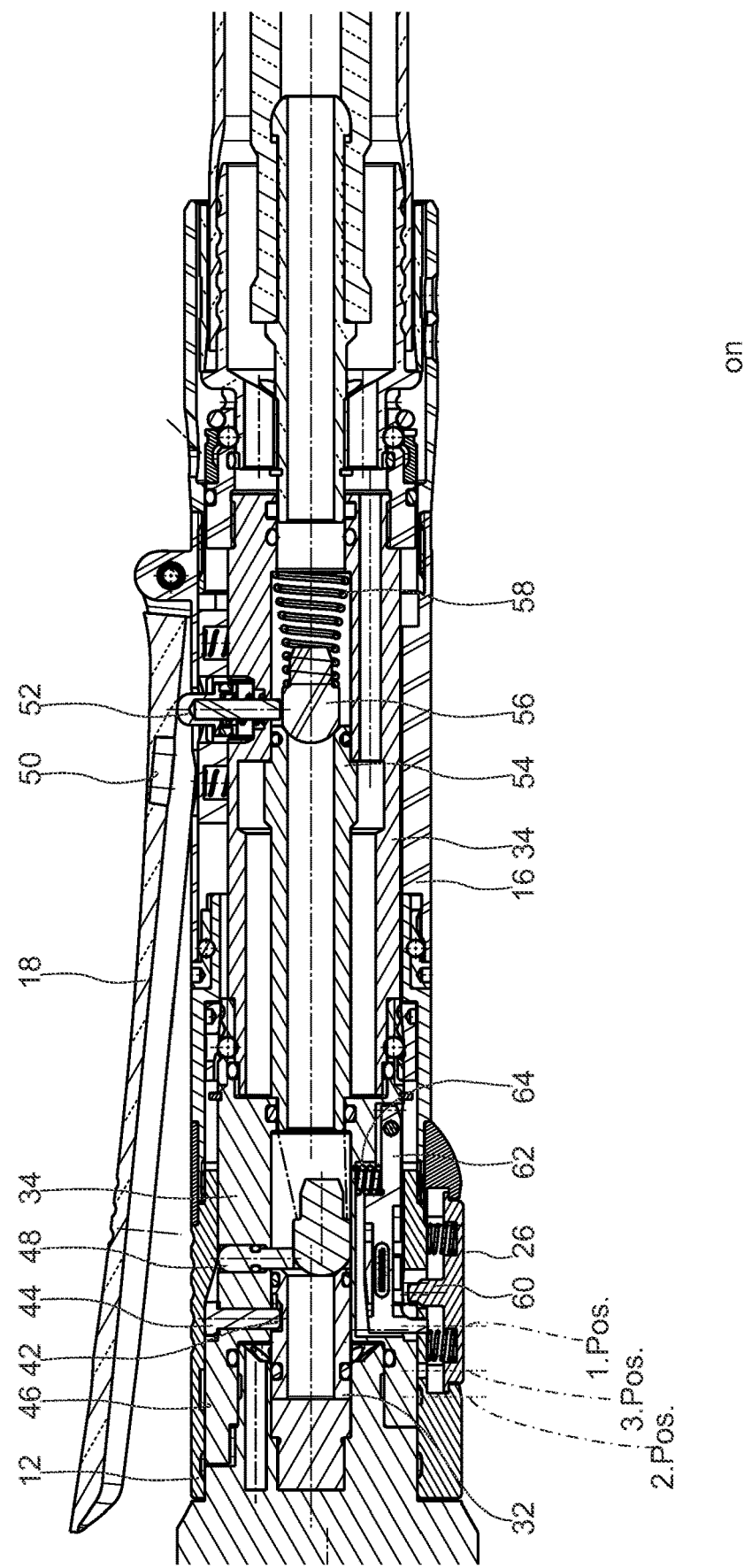
Figure 7:
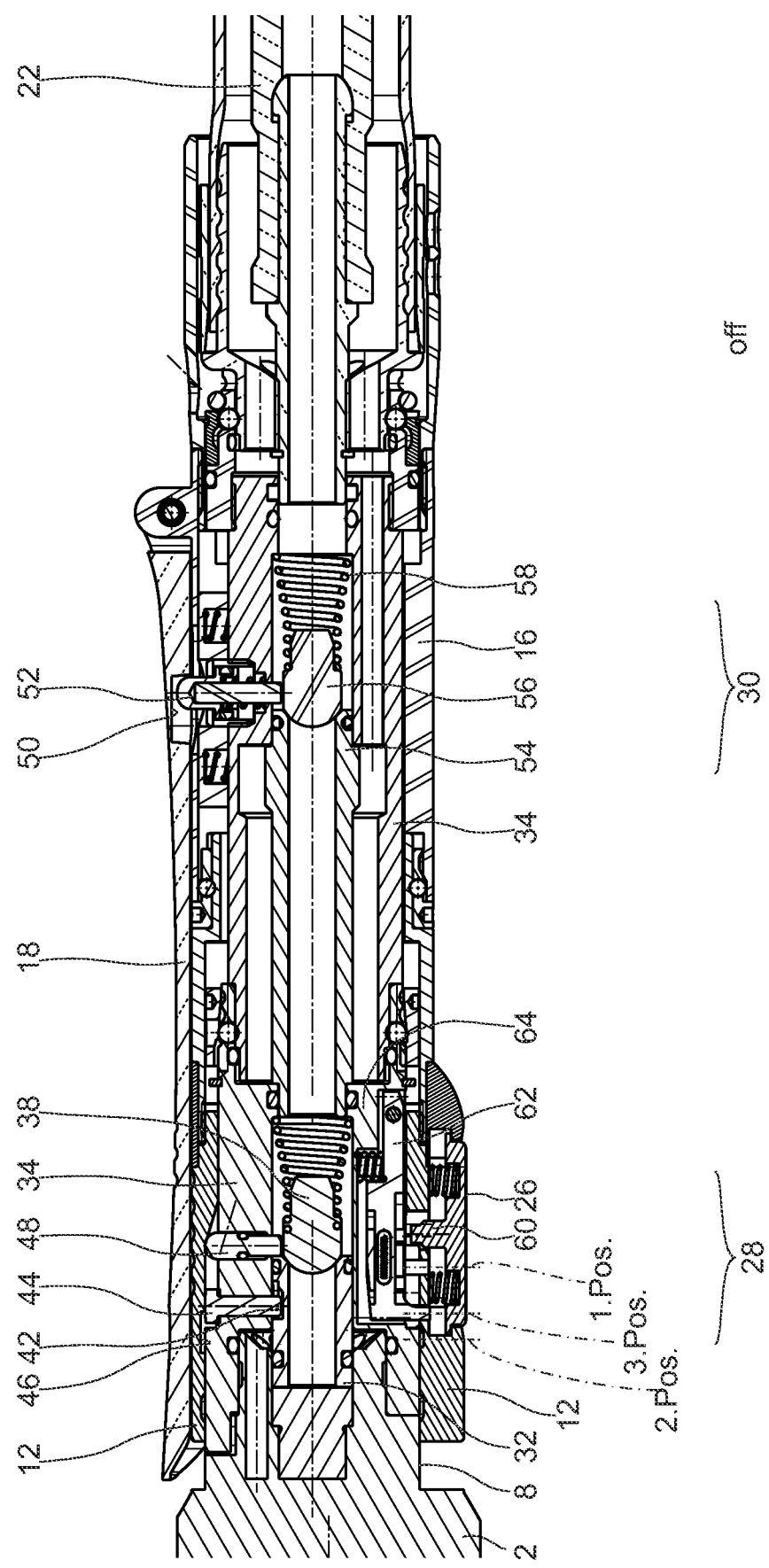
Figure 8:
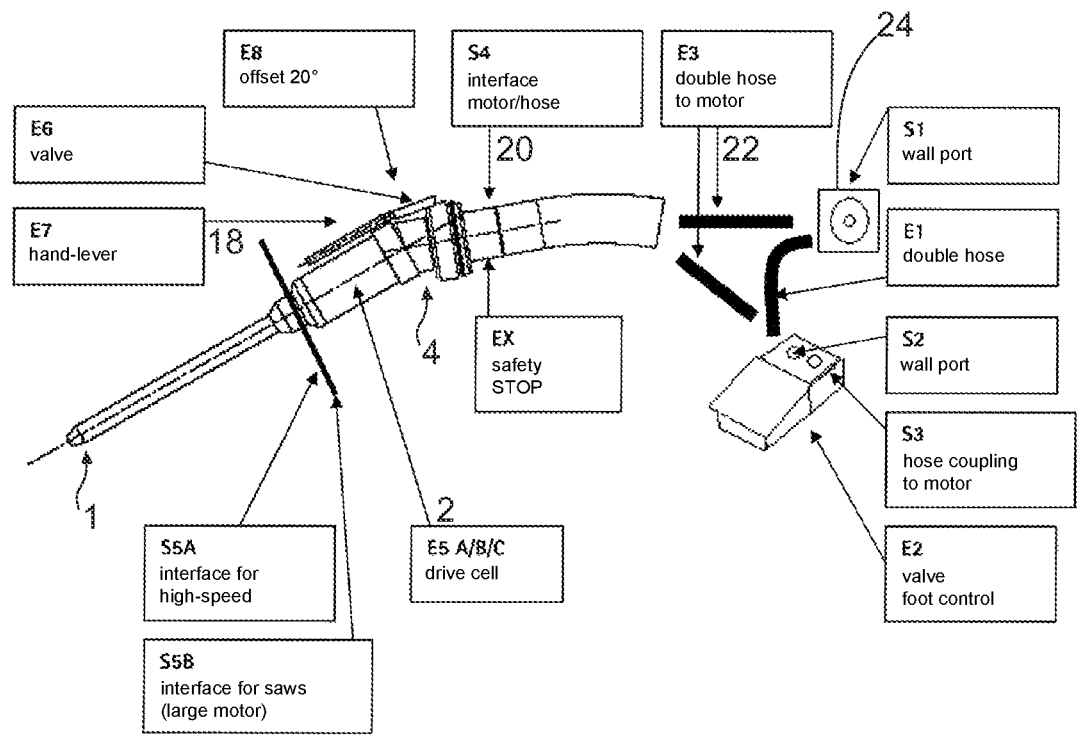

Hereinafter the invention will be explained in detail by way of a preferred embodiment with reference to the accompanying Figures, wherein:

FIG. 1a shows the side view of a medical/surgical instrument system according to a preferred embodiment of the invention, especially of a medical handle comprising an actuating element/actuator and an integrated regulating/control mechanism as well as of a surgical instrument and, resp., a motor unit thereof in the unlocked and uncoupled state according to a preferred embodiment of the present invention, FIG. 1b shows the top view of the handle according to FIG. 1a, FIG. 2 shows the longitudinal sectional view of the medical/surgical instrument system according to FIG. 1a, FIG. 3a shows an enlarged longitudinal sectional view of an unlocked and uncoupled clutch for fluidic and simultaneously mechanical coupling of the handle and the instrument/motor unit, FIG. 3b shows another enlarged longitudinal sectional view of an unlocked and uncoupled clutch for fluidic and simultaneously mechanical coupling of the handle and the instrument/motor unit, FIG. 4 shows the longitudinal sectional view of the medical/surgical instrument system according to FIG. 1a in the coupled and locked state with the first valve device being opened and the second valve device being put into function, FIG. 5a shows an enlarged longitudinal sectional view of the coupled and locked clutch for fluidic and simultaneously mechanical coupling of the handle to the instrument/motor unit according to FIG. 4, FIG. 5b shows another enlarged longitudinal sectional view of the coupled and locked clutch for fluidic and simultaneously mechanical coupling of the handle to the instrument/motor unit according to FIG. 4, FIG. 6 shows an enlarged fragmentary longitudinal sectional view especially of the handle when the clutch is coupled and locked with the first valve device being opened and the second valve device being put into function, FIG. 7 shows an enlarged fragmentary longitudinal sectional view especially of the handle when the clutch is coupled and locked with the first valve device being opened and the second valve device being put out of function ($3^{rd}$ actuating position and, resp., emergency stop position), and FIG. 8 shows the medical/surgical instrument system comprising all required elements.

DETAILED DESCRIPTION

In accordance with FIGS. 1a, 1b, 2 and 8, a medical/surgical instrument system generally comprises a medical instrument 1 either having an internal hydraulic/pneumatic motor or having an external/separate motor unit of the hydraulic/pneumatic design 2 and a medical handle 4 for pneumatically or hydraulically driven medical instruments or motor units. The handle 4 comprises at its distal end a preferably female clutch member 6 for mechanical and pneumatic/hydraulic coupling of a corresponding preferably male clutch member 8 on the side of the instrument 1 or of the upstream motor unit 2 and an internal manually operable valve mechanism or, resp., regulating/control valve mechanism 10 for selective pressurization of the medical instrument 1 coupled thereto or the upstream motor unit 2 thereof. The valve mechanism 10 inter alia includes a safety device or safety function for preventing pressurization, if the medical instrument 1 or the motor unit 2 thereof is unlocked and/or uncoupled.

The (female) clutch member 6 provided on the side of the handle 4 is designed so that it (mechanically) interacts with the valve mechanism 10 such that, during or by the mechanical coupling operation especially during or by locking the already coupled coupling member 6 by means of a manually operable clutch locking element 12, said valve mechanism is automatically/forcedly opened and/or enabled for (subsequent) manual opening, whereas in the unlocked and/or uncoupled state the valve mechanism 10 is closed and/or enabling is cancelled.

At this point, the technical terms used so far shall be defined as follows:

The medical/surgical instrument 1 relates, according to FIG. 8, to the portion of the instrument system in which a tool, for example a drill, a milling tool, a screwdriver etc. is supported. Where appropriate, the instrument 1 also accommodates a gear unit. Furthermore, the instrument 1 may include a mechanical clutch for connecting a separate motor unit. As an alternative, the instrument 1 may already be internally/integrally provided with a pneumatic/hydraulic motor.

The motor unit 2 relates to a usually cartridge-like motor block which is arranged upstream of the instrument 1. The motor block may be a separate unit and may optionally be mechanically coupled to the instrument 1 or to an interposed gear unit (not shown in detail).

The motor may include a turbine which is adapted to be rotated by way of compressed air. There may also be provided a pneumatic/hydraulic cylinder as a motor for an axial movement upon pressurization.

The handle 4 relates to the portion of the instrument system which is provided for manual operation of the instrument 1 as well as for holding the instrument 1. It is equipped with appropriate actuating means such as actuators for (on-off/amount of actuation-dependent) actuating an internal/integral valve mechanism 10, locking elements 12 for fluidic and mechanical coupling to the instrument/motor unit and/or emergency stop switch.

The uncoupled state is the state in which the handle 4 is disconnected from the instrument/motor unit 1 and 2, respectively.

The unlocked state is the state in which, although the handle 4 is coupled to the instrument/motor unit 1 and 2, the clutch is not yet locked, however, and thus can be easily uncoupled again.

The locked state is the state in which the coupled clutch members are locked and the clutch thus can be loaded with force.

In FIG. 1*a* the medical/surgical instrument system preferably of the pneumatic design is exemplified with a separate motor unit 2, with the instrument itself not being shown. For this purpose, it is referred to FIG. 8, however, where the instrument 1 is illustrated in the form of a rotary milling tool which is coupled already to a separate motor unit 2 as a drive cell.

In FIG. 1*a* the male clutch member 8 on the side of the motor unit 2 is visible which axially protrudes from the proximal end face of the motor unit 2 in the form of a nozzle. The nozzle internally forms a fluid channel having a fluid outlet in the direction of a motor turbine (not shown in detail). At the outer circumference of the nozzle at least one circumferential groove 14 is formed as an engaging/locking groove.

According to FIGS. 1*a* and 1*b*, the handle 4 is composed of an outer sleeve 16 at the distal axial portion of which the sleeve-shaped clutch locking element 12 is (integrally) formed or mounted. In a central portion of the outer sleeve a manually operable actuator 18 is hinged in the form of an actuating lever. In a proximal axial portion a hose port 20 is formed into which a preferably flexible pressure hose 22 is mounted preferably according to the Luer-lock principle. The hose 22 in turn is adapted to be connected to a pneumatic source 24 indicated in FIG. 8, for example in the form of a compressor or a stationary pneumatic ring line.

The actuating lever 18 in the present case serves for switching on-off (opening-closing) the valve mechanism 10 inside the handle 4 for selectively pressurizing the coupled and locked instrument/motor unit 1 and 2, respectively. It is also imaginable, however, to actuate the actuating lever 18 in a regulated manner comparable to a throttle control so as to regulate/control the supply of compressed air in response to the actuation amount.

At a position which is preferably diametrically opposed to the actuating lever 18 on the outer sleeve 16 and especially on the clutch locking element/portion 12 thereof a press switch or press button 26 is supported to be radially movable.

In FIG. 2 the interior (valve mechanism and regulating/control valve mechanism) of the handle 4 is shown at a glance. This will be described in detail hereinafter successively regarding the handle 4 from distal toward proximal with reference to the respective enlarged representations of FIGS. 3 to 7.

The valve mechanism 10 of the handle 4 according to the preferred embodiment of the present invention includes a first valve device 28 and second valve device 30 which are axially spaced from each other. The first valve device 28 is a valve operable exclusively via the clutch 6 and, resp., the clutch locking element 12 and preferably being designed as a seat valve, whereas the second valve device 30 is a valve operable via the actuator/actuating lever 18 and preferably being equally designed as a seat valve.

According to FIGS. 3*a* and 3*b*, the first valve device 28 is composed of a sleeve-shaped valve housing 32 which is supported to be axially movable in an inner sleeve 34 of the handle 4 which is relatively movably sheathed by the outer sleeve 16 and, resp., the clutch locking element 12 and at its distal end face protrudes into a receiving shaft 36 for the nozzle-type male clutch member 8 on the side of the instrument/motor unit. At the proximal end face of the valve housing 32 a mushroom-shaped or spherical valve body 38 is arranged which is biased against the valve housing 32 via a conical pressure spring 40 and thus axially seals the valve housing 32. The conical pressure spring 40 rests on an annular shoulder at the inner sleeve 34 of the handle 4.

On the outer circumferential surface of the valve housing 32 at least one circumferential groove 42 is incorporated as a backup groove. In the area of the backup groove 42 a detent pin 44 is provided which is supported to be radially movable in the inner sleeve 34. At its radially inner end face the detent pin 44 rests on the circumferential surface of the valve housing 32 and at its radially outer end face it is guided in an axial crank at the inner circumference of the clutch locking element 12.

The valve housing 32 and the clutch locking element 12 are adjusted to each other in terms of construction and position so that, when the male clutch member 8 is inserted in the receiving shaft 36 of the female clutch member 6, the inserted nozzle 8 axially displaces the valve housing 32 against the spring bias of the valve body 38 until the radial detent pin 44 slides into the backup groove 42 and, in so doing, releases the clutch locking element 12 at the inner crank guide thereof for an axial movement. When, on the other hand, the nozzle 8 is removed from the receiving shaft 36, the spring bias by means of the spring 40 axially forces the valve housing 32 somewhat into the receiving shaft 36, wherein the detent pin 44 is displaced out of the backup groove 42 radially outwards and engages in a groove 46 at the inner crank guide of the clutch locking element 12. Thus, in the uncoupled state of the clutch members 6, 8 the clutch locking element 12 cannot be axially moved relative to the inner sleeve 34 of the handle 4 any longer.

In other words, the afore-described mechanism serves for blocking actuation of the clutch locking element 12 by means of the detent pin 44 when the nozzle 8 is not inserted in the receiving shaft 36. The displacement of the valve housing 32 for actuation of the detent pin 44 constitutes only one constructional variant for this purpose. It is also imaginable to support the detent pin so that the latter is actuated directly by the nozzle 8 when the latter is inserted into the receiving shaft. In this context, also other constructional solutions are applicable.

Furthermore, in parallel to the detent pin 44 an actuating pin 48 is supported to be radially movable within the inner sleeve 34, said actuating pin 48 abutting with its inner end face against the valve body 32 and being received at its radially outer end face in the crank guide. The latter forms a radially inwards rising ramp in the area of the actuating pin 48 (cf. especially FIG. 6) such that, upon displacing the clutch locking element 12 in the distal direction for locking the clutch members 6, 8, the actuating pin 48 is moved radially inwards and, accordingly, forces the valve body 38 of the first valve device 28 radially away from the valve seat of the valve housing 32.

In other words, displacing of the clutch locking element 12 from the unlocking position according to FIG. 2 in the direction of the locking position e.g. according to FIG. 4 automatically and, resp., forcedly causes the first valve device 28 to be mechanically opened via the actuating pin 48.

As is further evident from FIG. 2, the actuating lever 18 is axially moved along, as it is hinged to the outer (movable) sleeve 16, during axial movement of the clutch locking element 12 as a distal portion of the outer sleeve 16 relative to the inner sleeve 34. That is, the actuating lever 18 automatically/forcedly varies its axial position relative to the inner sleeve 34 upon actuation of the clutch locking element 12.

The actuating lever 18 includes an axially extending recess or notch (blind hole) 50 on its lower side facing the outer sleeve 16. In said axial area a further actuating pin 52 is supported to be radially movable in the inner sleeve 16. The position of the lever 18 relative to the further actuating pin 52 is adjusted so that in an unlocking position of the clutch locking element 12 (cf. FIG. 2) the lever 18 adopts a relative position in which the further actuating pin 52 radially protrudes into the notch 50. That is to say, when in said relative position the lever 18 is pivoted toward the outside of the outer sleeve 16, the further actuating pin 52 freely immerses into the recess/notch 50 at the lever 18 without being radially displaced by the lever 18. Pivoting of the lever 18 thus is ineffective, as indicated in FIG. 2, for example.

When, on the other hand, the clutch locking element 12 is axially displaced to the (active) locking position thereof, the lever 18 automatically moves along. Accordingly, the further actuating pin 52 gets out of the area of the lever-side recess/notch 50, as indicated, for example, in FIG. 4. When in such axial relative position the lever 18 is pivoted towards the outer sleeve 16, it forces the further actuating pin 52 radially inwards.

Radially inside of the further actuating pin 52 the second valve device 30 is provided which is composed of a sleeve-type valve housing 54 at the proximal end face of which a spherical or mushroom-shaped valve body 56 is arranged, the latter being axially forced against an end-side valve seat at the valve housing 54 by means of a (conical) spring 58. The valve body 56 is positioned exactly radially beneath the further actuating pin 52 such that, upon displacement thereof to the radial inside, the valve body 56 is forced away from the valve seat and thus opens the second valve device 30.

Finally, in the area of the clutch locking element 12 the actuating button or the key 26 is supported to be radially movable at the outer sleeve 16.

The actuating head 26 includes an actuating finger or tappet 60 which abuts against a detent 62 pivotally supported on the inner sleeve 34. The detent 62 is biased by means of a spring 64 radially outwards against the outer sleeve 16 which in the area of the clutch actuating element/portion 12 includes at least two, preferably 3 axially spaced internal bores pos. 1 to pos. 3 in which the detent 62 engages, depending on the axial position of the outer sleeve 16 relative to the inner sleeve 34, in a spring-biased manner and thus fixes the adopted axial position.

The three axially spaced inner bores pos. 1 to pos. 3 relate to the individual actuating positions of the clutch locking element, as will be described in the following:

The internal bore pos. 1 relates, according to FIG. 6, to the actuating position in which the coupled clutch members 6, 8 are locked by means of the clutch locking element 12 and, at the same time, the first valve device 26 is opened and the second valve device 30 is enabled. This position is referred to as active locking position.

The internal bore pos. 3 relates, according to FIG. 7, to the actuating position in which the coupled clutch members 6, 8 are locked by means of the clutch locking element 12 and, at the same time, the first valve device 26 is opened and the second valve device 30 is not enabled, however. That is, the further actuating pin 52 is still provided inside the recess/notch 50 in the case of pivoting of the lever 18. This position is referred to as a passive locking position, as the clutch is locked but the valve mechanism 10 cannot be actuated. The passive locking position optionally also constitutes the position which, upon pressing the actuating button 26 while coming from the active locking position, is adopted preferably automatically by an axial spring bias so as to interrupt the compressed air supply in the case of emergency without the lever 18 having to be released. The passive locking position therefore can also be referred to as emergency stop position.

The internal bore pos. 2 relates, according to FIG. 2, to the actuating position in which the clutch members 6, 8 are unlocked, wherein the first valve device 26 is closed and the second valve device 30 is not enabled.

It is outlined in this context that the internal bore pos. 3 represents an optional advantageous measure. The handle 4 according to the invention theoretically could execute its basic functions even without said internal bore. It is further referred to the fact that all those features that have been listed at the beginning of the description concerning the prior art which is to be further developed according to the invention are technically materialized also in the present invention so that the repeated description thereof can be renounced here.

Hereinafter the function of the medical handle according to the invention and, resp., of the medical instrument system according to the invention will be described in detail.

At first, the pressure hose 22 including the handle 4 mounted thereon is connected to the compressed medium source 24 so that the handle 4 is pressurized immediately thereafter. In this phase, the outer sleeve 16 is displaced relative to the inner sleeve 34 of the handle 4 in the proximal direction, wherein the detent 62 is engaged in a spring-biased manner in the internal bore pos. 2 at the clutch locking element 12. Thus, the handle 4 adopts the unlocking position in which the first valve device 28 is closed and the second valve device 30 is not enabled. Moreover, this position is fixed by the detent pin 44 which is forced radially outwards into the internal groove 46 of the clutch locking element 12 via the valve housing 32 of the first valve device 28. In this operating position, the clutch locking element 12 cannot be axially displaced. Although actuation of the lever 18 is possible, it is ineffective as the further actuating pin 52 would immerse into the recess/notch 50 at the lever 18 and therefore cannot be axially displaced.

Even if the lever 18 was pivoted away from the outer sleeve 16 or broken off so that direct manual actuation of the further actuating pin 52 would be possible, the functional safety can be continued to be guaranteed, as the first valve device 28 is closed in any case.

As soon as the instrument 1 or the separate motor unit (drive cell) 2 thereof is inserted via the clutch nozzles 8 thereof into the receiving shaft 36 of the handle-side clutch 6, the valve housing 32 of the first valve device 28 is axially displaced, wherein the detent pin 44 slides out of the internal groove 46 of the clutch locking element 12 into the backup groove 42 at the valve housing 32 and in this way releases the clutch locking element 12 for manual axial displacement thereof. Now the clutch locking element 12 may be axially displaced in the distal direction until the detent 62 pivoted on the inner sleeve 34 engages in the internal bore pos. 2 and the outer sleeve 16 fixes the clutch locking element 12 in the active locking position.

In this position, the actuating pin 4 of the first valve device 28 is displaced radially inwards from the clutch locking element 12 and forces the valve body 38 of the first valve device 28 away from the valve seat. The first valve device thus is opened. At the same time, the actuating lever/actuator 18 is displaced in the distal direction such that the further actuating pin 52 of the second valve device 30 gets out of the area of the recess/notch 50 in the lever 18. When now the lever 18 is pivoted against the outer sleeve 16 of the handle 4, the lever 18 abuts on the radially outer end face of the further actuating pin 52. With further pivoting of the actuating lever 18 the further actuating pin 52 moves radially inwards and forces the valve body 56 of the second valve device 30 away from the valve seat thereof. In this way, also the second valve device 30 is opened and the instrument/motor unit is pressurized with pressurizing medium.

The second valve device may be an open-closed valve or a regulating valve which regulates the amount of pressurized medium per time unit in response to the actuating degree of the lever 18. Alternatively to the shown seat valve, for the second valve device, but also for the first valve device where necessary, a slide valve is imaginable.

In order to be able to uncouple the instrument again at first the lever 18 has to be released, wherein the second valve device closes. Hereupon the press button 26 is pressed so that the detent/engaging pawl disengages from the internal bore pos. 2 at the outer sleeve 16 and, resp., at the clutch locking element 12 and releases the clutch locking element 12 for an unlocking movement. When the clutch locking element 12 is then displaced axially in the proximal direction, the detent 62 engages in the internal bore pos. 1 upon reaching the uncoupling position and there fixes the clutch locking element 12. In this position, the actuating pin 48 is released and the valve body 38 has returned to its valve seat. Hence the first valve device 28 is closed.

If now the nozzle 8 of the instrument/motor unit 2 is removed from the receiving shaft 36, the valve housing 32 of the first valve device 28 moves somewhat into the receiving shaft 32 while being spring-biased and, accordingly, forces the detent pin 44 into the inner groove 46 at the clutch locking element 12. In this way, the clutch locking element 12 is axially locked so that the first valve device 28 cannot be opened any longer.

In a case of emergency with the lever 18 being actuated, the press button 26 can be pressed whereupon the detent 62 is forced out of the internal bore pos. 2 and the clutch locking element 12 is moved in the proximal direction possibly automatically by suitable axial spring bias (not shown in detail) or by manual displacement, until the detent 62 snaps into the (axially central) internal bore pos. 3 while being spring-biased and there fixes the clutch locking element 12. In this actuating position (passive locking position) the clutch continues to be locked, but the lever 18 is displaced relative to the inner sleeve 34 so far that the further actuating pin 52 already slides into the recess/notch 50 at the lever 18 and therefore no longer can be displaced via the lever.

Finally, it may be referred to the clutch locking mechanism which can be actuated by the clutch locking element 12.

In the simplest case, the clutch locking mechanism according to FIG. 3a, 3b or 5a, 5b, for example, is the arrangement of plural (preferably four) engaging elements 70 (balls, pins etc.) which are supported to be radially movable in radial bores on the inner sleeve 34 which in turn are spaced apart in the circumferential direction. Said engaging elements 70 are spring-biased radially inwards and somewhat protrude into the receiving shaft 32.

When thus the nozzle 8 is inserted into the receiving shaft 32 at the instrument/motor unit 2, the engaging elements 70 are first displaced radially outwards and finally snap into the groove 14 at the nozzle 8 while being spring-biased.

In this operating position, the nozzle 8 is held ready in the receiving shaft 32, wherein the clutch connection is not loadable with force, however. That is, the nozzle 8 can be removed from the receiving shaft 32 again while overcoming the spring bias onto the engaging elements 70. However, as soon as the clutch locking element 12 has been displaced in the distal direction, it encompasses the engaging elements at the outer circumference of the inner sleeve 34 and, in this way, suppresses a displacing movement of the engaging element 70 radially outwards. Now the clutch is locked.

The invention claimed is:

1. A medical handle for a pneumatically or hydraulically driven medical instrument, the medical handle comprising:
   a clutch member on a side of the medical handle for mechanical and pneumatic/hydraulic coupling of a corresponding clutch member on a side of the pneumatically or hydraulically driven medical instrument; and
   a manually operable valve mechanism for selective pressurization of the pneumatically or hydraulically driven medical instrument coupled thereto or the motor unit thereof, which medical handle is equipped with a safety function for preventing pressurization when the pneumatically or hydraulically driven medical instrument or a motor unit thereof is uncoupled,
   wherein the clutch member present on the side of the medical handle interacts with the valve mechanism such that during or by a mechanical coupling operation, the valve mechanism is automatically opened or enabled for manual opening, whereas correspondingly in an uncoupled state, the valve mechanism is closed or enabling is correspondingly cancelled, wherein the clutch member on the side of the medical handle is provided with or interacts with a first valve device of the valve mechanism, the first valve device being designed so that it is automatically opened at the latest by/during pressure-tight locking of the clutch member on the side of the medical handle, and wherein the clutch member on the side of the medical handle interacts with a second valve device of the valve mechanism such that the second valve device is operative for manual opening and closing only in a state in which the clutch member is coupled and locked and is inoperative in a state in which the clutch member is uncoupled.

2. The medical handle according to claim 1, wherein the valve mechanism includes a manually operable actuator which directly or indirectly acts on the second valve device for selective opening thereof, wherein by or upon locking the clutch member on the side of the medical handle the functioning of the actuator is automatically brought about and at least by or upon unlocking the clutch member the actuator is rendered incapable of acting on the second valve device for selective opening thereof.

3. The medical handle according to claim 2, wherein a manually operable clutch locking element of the clutch member being movably supported on the medical handle is operatively connected mechanically to at least one of the first valve device and the actuator so that manual operation of the clutch locking element automatically causes at least one of: (a) the first valve device to open/close and (b) exerts an appropriate effect on the actuator such that the actuator is capable/incapable of acting on the second valve device for selective opening thereof.

4. The medical handle according to claim 3, wherein the actuator is moved along upon/by unlocking the clutch member by the clutch locking element so that the operative connection to the second valve device is disconnected, or in that upon unlocking the clutch member by the clutch locking element a stop is moved into an operating path of the actuator.

5. The medical handle according to claim 3, wherein, for the clutch locking element, a plurality of operating positions are provided comprising a first operating position as an unlocking position for uncoupling the medical handle from the instrument/motor unit, a second operating position as an active locking position for locking the coupled clutch members while simultaneously opening the first valve device and putting the second valve device into function, and a third operating position as a passive locking position for locking the clutch members while simultaneously opening the first valve device and putting the second valve device out of function.

6. The medical handle according to claim 5, wherein the medical handle comprises a push button or switch in an area of the clutch locking element upon actuation of which the clutch locking element is shifted due to axial bias from the second operating position to the third operating position.

7. The medical handle according to claim 6, wherein the third operating position is located in an operating path between the first operating position and the second operating position.

8. A medical instrument system comprising a hydraulically or pneumatically operated medical instrument or a motor unit thereof on which a clutch member is arranged for mechanical and hydraulic/pneumatic coupling to a clutch member on a medical handle which is adapted to be connected to a pneumatic source via a pneumatic hose, wherein the medical handle comprises the medical handle of claim 1.

9. The medical instrument system according to claim 8, wherein upon insertion in a female clutch member, a male clutch member automatically actuates a stop element for releasing a clutch locking element for selective manual locking of the female clutch member when the male clutch member is coupled.

10. A medical handle for a pneumatically or hydraulically driven medical instrument, the medical handle comprising:
a clutch member on a side of the medical handle for mechanical and pneumatic/hydraulic coupling of a corresponding clutch member on a side of the pneumatically or hydraulically driven medical instrument; and
a manually operable valve mechanism for selective pressurization of the pneumatically or hydraulically driven medical instrument coupled thereto or the motor unit thereof, which medical handle is equipped with a safety function for preventing pressurization when the pneumatically or hydraulically driven medical instrument or a motor unit thereof is uncoupled,
wherein the clutch member present on the side of the medical handle interacts with the valve mechanism such that during or by a mechanical coupling operation, the valve mechanism is automatically opened or enabled for manual opening, whereas correspondingly in an uncoupled state, the valve mechanism is closed or enabling is correspondingly cancelled,
wherein the clutch member on the side of the medical handle interacts with a manually operable valve device of the valve mechanism such that the valve device is operative for manual opening and closing only in a state in which the clutch member is coupled and locked and is inoperative in a state in which the clutch member is uncoupled.

11. The medical handle according to claim 10, wherein the valve mechanism includes a manually operable actuator, wherein by or upon locking the clutch member on the side of the medical handle the functioning of the actuator is automatically brought about such that the actuator is capable of acting directly or indirectly on the valve device for selective opening thereof and at least by or upon unlocking the clutch member the actuator is put out of function such that the actuator is incapable of acting on the valve device for selective opening thereof.

12. The medical handle according to claim 11, wherein a manually operable clutch locking element of the clutch member being movably supported on the medical handle is operatively connected mechanically to the actuator of the valve device so that manual operation of the clutch locking element exerts an appropriate effect on the functioning of the actuator such that the actuator is capable/incapable of acting on the valve device for selective opening thereof.

13. The medical handle according to claim 12, wherein the actuator is moved along upon/by unlocking the clutch member by the clutch locking element to a position in which the operative connection to the valve device is disconnected, or in that upon unlocking the clutch member by the clutch locking element a stop is moved into an operating path of the actuator.

14. A medical handle for a pneumatically or hydraulically driven medical instrument, the medical handle comprising:
a clutch member on a side of the medical handle for mechanical and pneumatic/hydraulic coupling of a corresponding clutch member on a side of the pneumatically or hydraulically driven medical instrument; and a manually operable valve mechanism for selective pressurization of the pneumatically or hydraulically driven medical instrument coupled thereto or the motor unit thereof, which medical handle is equipped with a safety function for preventing pressurization when the pneumatically or hydraulically driven medical instrument or a motor unit thereof is uncoupled, wherein the clutch member present on the side of the medical handle interacts with the valve mechanism such that during or by a mechanical coupling operation, the valve mechanism is automatically opened or enabled for manual opening, whereas correspondingly in an uncoupled state, the valve mechanism is closed or enabling is correspondingly cancelled, wherein the clutch member on the side of the medical handle is provided with or interacts with a first valve device of the valve mechanism, the first valve device being designed so that it is automatically opened at the latest by/during pressure-tight locking of the clutch member on the side of the medical handle.

15. The medical handle according to claim 14, wherein a manually operable clutch locking element of the clutch member being movably supported on the medical handle is operatively connected mechanically to the valve device so that manual operation of the clutch locking element automatically causes the valve device to open/close.

* * * * *